United States Patent [19]

Kurono et al.

[11] Patent Number: 5,428,015
[45] Date of Patent: Jun. 27, 1995

[54] VASOACTIVE INTESTINAL POLYPEPTIDE ANALOGUES AND USE THEREOF

[75] Inventors: Masayasu Kurono; Takahiko Mitani; Haruo Takahashi; Kiichi Sawai, all of Aichi, Japan

[73] Assignee: Sana Kagaku Kenkyusho Co., Ltd., Aichi, Japan

[21] Appl. No.: 201,092

[22] Filed: Feb. 24, 1994

Related U.S. Application Data

[63] Continuation of Ser. No. 704,143, May 22, 1991, abandoned.

[30] Foreign Application Priority Data

Jun. 26, 1990 [JP] Japan .................. 2-165739
Dec. 27, 1990 [JP] Japan .................. 2-408425

[51] Int. Cl.$^6$ .................. C07K 7/08; A61K 37/02
[52] U.S. Cl. .................. 514/12; 530/324
[58] Field of Search .................. 530/324; 514/12

[56] References Cited

U.S. PATENT DOCUMENTS

| | | | |
|---|---|---|---|
| 3,880,826 | 4/1975 | Said et al. .................. | 530/324 |
| 4,757,133 | 7/1988 | Ito et al. .................. | 530/324 |

FOREIGN PATENT DOCUMENTS

| | | |
|---|---|---|
| 0259891 | 3/1988 | European Pat. Off. . |
| 0378078 | 7/1990 | European Pat. Off. . |
| 56-128721 | 10/1981 | Japan . |
| 62-16429 | 1/1987 | Japan . |
| 62-116595 | 5/1987 | Japan . |
| 62-246595 | 10/1987 | Japan . |
| 63-179892 | 7/1988 | Japan . |
| 64-83012 | 3/1989 | Japan . |
| 1-296996 | 11/1989 | Japan . |
| 2-76821 | 3/1990 | Japan . |

OTHER PUBLICATIONS

"Peptides", vol. 6, pp. 597–601, 1985.
"Microbiol. Immunol.", vol. 22, No. 2, pp. 89–101, 1978.

*Primary Examiner*—Robert J. Hill, Jr.
*Assistant Examiner*—S. G. Marshall
*Attorney, Agent, or Firm*—Nikaido, Marmelstein, Murray & Oram

[57] ABSTRACT

Vasoactive intestinal polypeptide (VIP) analogues and use thereof are disclosed. The VIP analogues are shown by the formula of

His-Ser-Asp-Ala-Val-Phe-Thr-Asp-Asn-Tyr-Thr-Arg-Leu-Arg-Lys-Gln-X-Ala-Val-Lys-Lys-Tyr-Leu-Asn-Ser-Ile-Leu-Asn-Y wherein X is a residue of amino acid other than methionine (Met); and Y is homoserine, homoserine-lactone, amidized homoserine, a residue reacted homoserine-lactone with a primary alkyl amine having carbon atoms not exceeding 20, or an optional polypeptide chain and containing an amidized homoserine at C-terminal.

Each of the VIP analogues is employed as an effective ingredient for various medicines and a hair tonic, and more particularly curing an asthma and impotence.

2 Claims, 4 Drawing Sheets

↓ : Add Histamine ($10^{-5}$M)

⇓ : Add [L-Leu$^{17}$]-VIP-Hse ($10^{-7}$M)

FIG. 3B

↓ : Add Histamine ($10^{-5}$M)

↓ : Add native VIP ($10^{-7}$M)

FIG. 4A

↓ : Add Histamine ($10^{-5}$ M)

⇓ : Add [L-Leu$^{17}$]-VIP-Hse ($10^{-8}$ M)

FIG. 4B

↓ : Add Histamine ($10^{-5}$ M)

⇣ : Add native VIP ($10^{-8}$ M)

VASOACTIVE INTESTINAL POLYPEPTIDE ANALOGUES AND USE THEREOF

This application is a continuation of application Ser. No. 07/704,143, filed May 22, 1991, now abandoned.

BACKGROUND OF THE INVENTION

1. Field of the Invention

The present invention relates to a vasoactive intestinal polypeptide (hereinafter referred abbreviately to as "VIP") analogue, namely a novel polypeptide with biological activities as in "vasoactive intestinal polypeptide", and use thereof.

The VIP analogue according to the invention can be used as an effective ingredient For various medicines, for instance an agent for curing asthma, anaphylaxis, hyperpiesia, impotence and the like, as well as a hair tonic.

2. Related Arts

The VIP is one of peptide hormones and firstly isolated and refined by Said and Mutt in the year of 1970 from a subfraction, when secretin was extracted from a tissue of porcine upper small intestine. In 1974, a primary amino acid structure of the VIP has been made apparent as consisting of 28 amino acids and it has been considered that It belongs to a glucagonsecretin family.

Structure of the native VIP (SEQ ID NO:1)

Structure of the native VIP (SEQ ID NO: 1):

```
              5                          10
His—Ser—Asp—Ala—Val—Phe—Thr—Asp—Asn—Tyr—Thr—Arg—Leu—

15       17        20                  25
Arg—Lys—Gln—Met—Ala—Val—Lys—Lys—Tyr—Leu—Asn—Ser—Ile—

28
Leu—Asn—NH₂
```

It has been confirmed that the VIP presents in nervous systems in addition to the digestive canal to develop various biological activities, for instance a relatively high vasodilating-hypotensing action; atonic action on smooth muscle; accelerating action of intestinal juice secretion, pancreatic juice and bile secretions, and tear secretion; suppressing action of gastric juice secretion; accelerating action of glycogen decomposition; accelerating action of various pituitary hormone secretions; increasing action of blood flow into penis; vasodilating action of bronchus; anti-allergic action; antitumor action; growing action of hair and others.

Following patent literatures have been issued in Japan on the VIP, VIP analogues and use thereof.

a) Jap. Pat. No. Sho 56 128721(A), Anti-allergic agent;
b) Jap. Pat. No. Sho 62-16429(A), Acceleration of tear secretion;
c) Jap. Pat. No. Sho 62-116595(A), Anti-tumor and ulcer agent;
d) Jap. Pat. No. Sho 62-246595(A), Bronchodilatation agent and hypotensor;
e) Jap. Pat. No. Sho 63-1799892(A), Preparation of VIP-HCl unstable to acids;
f) Jap. Pat. No. Sho 64-83012(A), An agent for growing hairs;
g) Jap. Pat. No. Hei 1-296996(A), Hypotensor; and
h) Jap. Pat. No. Hei 2-76821(A), External preparation for curing impotence.

Among of those biological activities, the VIP has been expected as the drugs for curing an asthma and impotence, by utilizing the bronchodiliatating action and the atonic action on smooth muscle of corpus cavernosum, respectively. A structural characteristic of the VIP lies in that there is an amide structure at C-terminal, which has been estimated as an indispensable matter for developing the biological activities of VIP.

For obtaining a polypeptide having an amide structure at C-terminal in accordance with conventional and widely accepted techniques which utilize a expression microorganism such as Escherichia coli, in general, it is required to separate and purify an expressed polypeptide and then to treat the polypeptide with use of a special C-terminal amidation enzyme. However, such an enzymatic method can not be said as that suitable for industrial scale production, since such enzyme is expensive and yield of the objective polypeptide becomes low.

Although there is no relation to the VIP in question, the inventors have found that on motilin analogues accelerating a peristalsis of intestines, those with homostrine or homoserine-lactone at C-terminal show biological activities in same level with or higher than the native motilin, and they have proposed a process for preparing such motilin analogues with a reasonable cost and in a large amount [Jap. Pat. Appln. No. Sho 64 (1989) 286, corresponding to a part of U.S. Ser. No. 07/459236 and EP-03 78 078(A1)].

Further, it has been reported that a chemically synthesized VIP analogue—methionine residue at 17th position of the native VIP being substituted with leucine or norleucine—shows biological activities similar to the native VIP [said Jap. Pat. No. Sho 62-246595(A)]. Therefore, it has been considered that the methionine residue at 17th position has almost no influence on useful activities of the VIP.

Hitherto, it has been considered as quite difficult to provide the VIP or VIP analogues with a reasonable price and in a large amount, since according to the prior arts, there is no way other than utilizing a synthetic process therefor or an extraction method thereof from an animal tissue, and the former requires troublesome operations due to that the VIP is polypeptide consisting of 28 amino acids, and takes a relatively long period of time in its chemical synthesis and for purifying the same, and the latter is restricted on availability of the raw material and requires troublesome purification procedures.

Further, the technique utilizing so-called "Biotechnology" can not be said as—convenient method—, since it requires a special technique for the amidation at C-terminal, as referred to hereinbefore.

SUMMARY OF THE INVENTION

A main object of the invention is to provide a VIP analogue with biological activities in same level with or higher than native VIP, by chemically synthesizing a polypeptide with a VIP-like structure, cleaving the resulting polypeptide with cyanogen bromide to prepare another polypeptide with homoserine (inclusive of homoserine-lactone) at C-terminal and VIP-like structure, and if necessary carrying out a simple chemical reaction thereon.

An additional but important object of the invention is to provide a pharmaceutical composition for curing various diseases, and more particularly asthma and impotence, which contains as an effective ingredient the VIP analogue.

The inventors have energetically studied and investigated on polypeptides obtained through a fermentation method or chemical synthesis and with a VIP-like structure. As a result, they have found that a polypeptide obtained through the cleaving step using cyanogen bromide has homoserine residue (inclusive of homoserine-lactone residue) at C-terminal and shows desired biological activities, and that an amide or alkyl amine can easily be bond to the residue in accordance with a conventional synthetic method, to establish the invention.

Therefore, according to the invention, problems in the prior arts can be dissolved by a VIP analogue shown by the general formula of (SEQ ID NO:2)

His-Ser-Asp-Ala-Val-Phe-Thr-Asp-Asn-Tyr-Thr-Arg-Leu-Arg-Lys-Gln-X-Ala-Val-Lys-Lys-Tyr-Leu-Asn-Ser-Ile-Leu-Asn-Y wherein X is a residue of amino acid other than methionine (Met); and Y is homoserine, homoserine-lactone, amidized homoserine, a residue reacted homoserine-lactone with a primary alkyl amine having carbon atoms not exceeding 20, or an optional polypeptide chain and containing an amidized homoserine at C-terminal, to attain the main object as referred to.

The ground of that the symbol "X" at 17th position amino acid residue is stated as the residue of amino acid other than methionine (Met) lies in that if X is Met residue, the desired polypeptide having the VIP-like activities can not be obtained, since a cleavage will also occur at Met in 17th position, when a fused protein is treated with the cyanogen bromide.

The additional object as referred to can be attained by a pharmaceutical composition :for curing various diseases, which contains as an effective ingredient at least one of the VIP analogues, in an effective amount.

DETAILED DESCRIPTION OF PREFERRED EMBODIMENTS

The invention will now be further explained in more detail with reference to Manufacturing Example, Pharmacological Test Examples as well as Medicine Preparation Examples.

EXAMPLE (Synthesis of VIP analogues)

In the first place, a polypeptide encoding the following amino acid sequence was synthesized with use of a peptide synthesizer (Type 430A marketed by Applied Biosystems Co.). (SEQ ID NO:3)

His-Ser-Asp-Ala-Val-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-Met-Ala-Ser

A purification of the synthesized polypeptide was carried out by subjecting to HPLC with use of a μ bondasphere C-18 column (19 mm×15 cm) marketed by Waters Co.

The resulting purified sample (10 mg) was taken and dissolved in 70% formic acid solution (30 ml). After added 50 mg of cyanogen bromide, the solution was kept for 24 hours at 37° C. to cause a reaction. Then, distilled water (200 ml) was added to the reaction mixture and lyophilized to remove the formic acid and cyanogen bromide. The resulting material was subjected again to HPLC under the following conditions, with use of the μ bondasphere C-18 column (19 mm×15 cm) marketed by Waters Co. to remove the protection group and resinous materials.

Elute: Linear gradient of 15% to 50% acetonitrile in 0.1% trifluoroacetic acid (30 minutes), Flow rate: 7.0 ml/min.

Fractions In a main peak part on the HPLC were recovered and lyophilized. Through said proceedings, the synthesized polypeptide encoding said amino acid sequence has been cleaved at methionine residue part at 29th position and it has been modified into homoserine or homoserine-lactone residue at C-terminal.

The polypeptide ([L-Leu$^{17}$]-VIP-Hse) was further treated with an acid (for instance, in 0.1N HCl at 30° C. for 3 hours) and then lyophilized, to convert homoserine residue at C-terminal into the homoserine-lactone residue in the level of 70% or more.

A part of the resulting VIP analogue was taken and checked with use of a peptide sequencer marketed by Applied Biosystems Co. to confirm that the initially synthesized polypeptide is cleaved at correct position of methionine residue at 29th position and there is the homoserine residue at C-terminal.

The polypeptide with the homoserine-lactone residue at C-terminal was collected through HPLC and lyophilized. The resulting dried powder was treated with 10% ammonia in dimethylformamide solution at room temperature for 24 hours to prepare a desired VIP analogue with homeserine-amide residue at C-terminal ([L-Leu$^{17}$]-VIP-Hse-NH$_2$).

Another type VIP analogue with an alkyl amine residue at C-terminal was prepared by reacting the polypeptide with homoserine-lactone residue at C-terminal with $CH_3(CH_2)_9NH_2$, $CH_3(CH_2)_{19}NH_2$ or the like primary alkyl amine, in dimethylsulfoxide solution.

Biological Activity Test Example 1

(Inhibition of bronchus contraction)

An inhibition of bronchus contraction was measured in accordance with a so-called "Magnus method" as disclosed in "Peptides", Vol. 6, pages 597–601 (1985) which uses an airway smooth muscle of guinea pig, on the VIP analogues {[L-Leu$^{17}$]-VIP-Hse-NH$_2$, [L-Leu$^{17}$]-VIP-Hse-NH(CH$_2$)$_9$CH$_3$ and [L-Leu$^{17}$]-VIP-Hse-NH(CH$_2$)$_{19}$CH$_3$}, as Test Samples and a marketed pure VIP, as Control Sample [Each of the airway smooth muscles were toned with histamine (Conc.: 10$^{-5}$M)].

Figure 1:
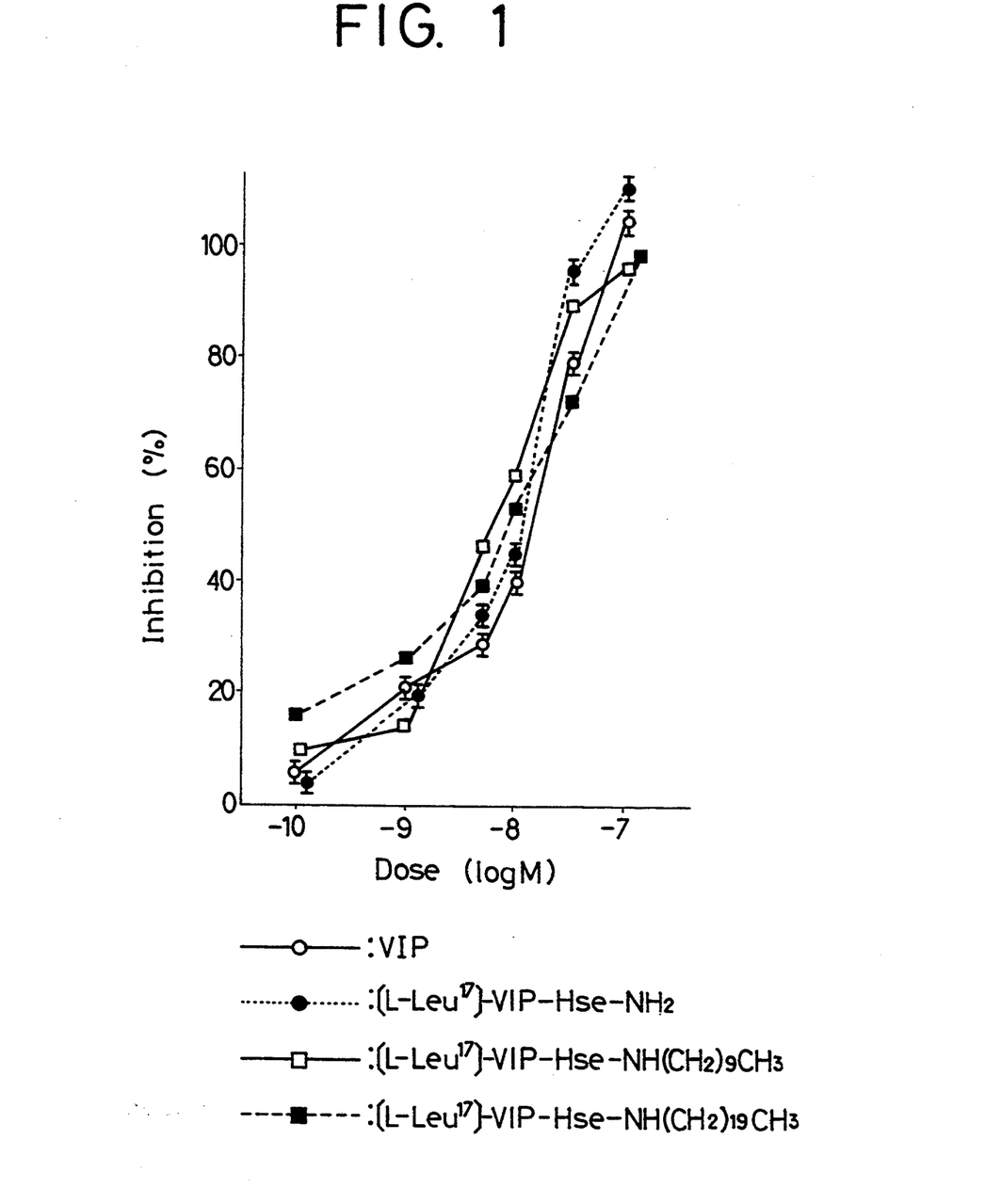
FIG. 1 is a graph showing results of measurements on reluxant activity In isolated guinea pig airway smooth muscle, in accordance with Magnus method, which reluxation is caused by VIP analogues (test samples) according to the invention, and by a pure VIP (control sample) prepared by a chemical synthesis.

Results are shown in FIG. 1. From the Figure, it is apparent that the VIP analogues according to the invention show the inhibition substantially equal to that of the native VIP.

Biological Activity Test Example 2

(Inhibition of bronchus contraction)

An inhibition of bronchus contraction was measured as described in the Biological Activity Test Example 1, but on the VIP analogue of [L-Leu$^{17}$]-VIP-Hse, as Test Sample.

Figure 2:
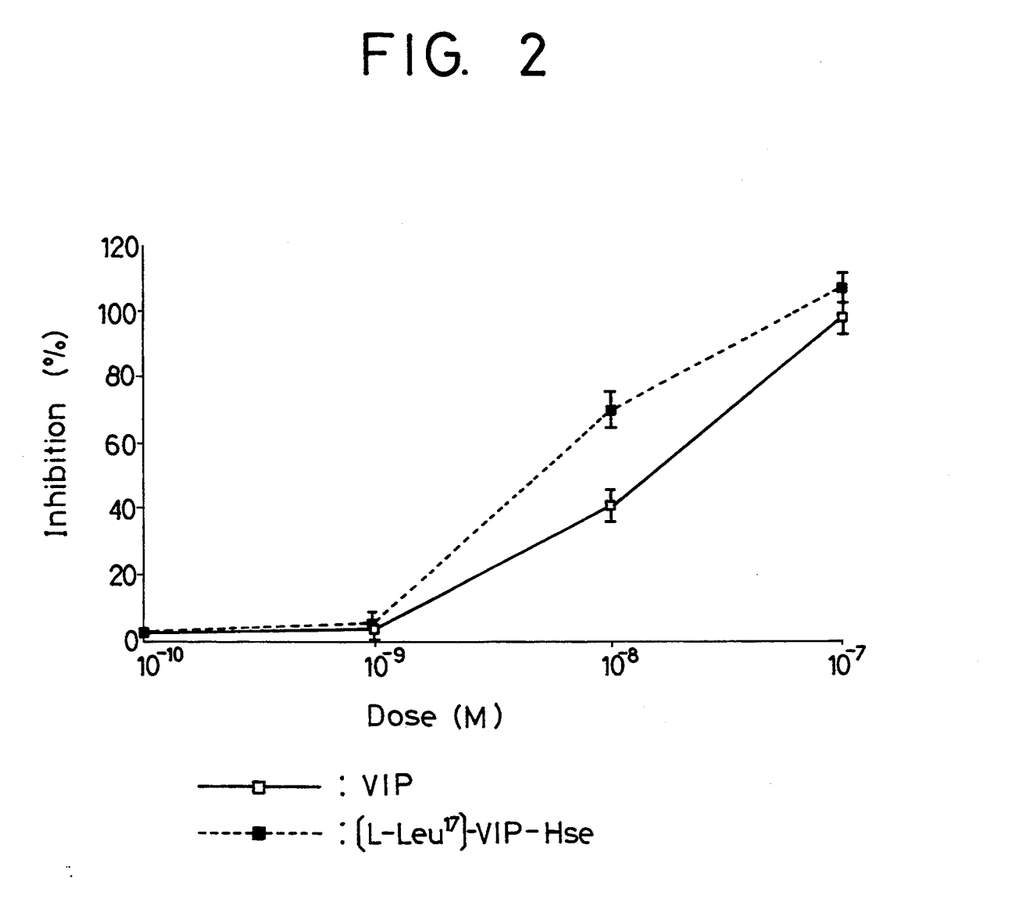
FIG. 2 is a graph similar to FIG. 1, excepting that test sample of VIP analogue is [L-Leu$^{17}$]-VIP-Hse.

Results are shown in FIG. 2.

Figure 3A:
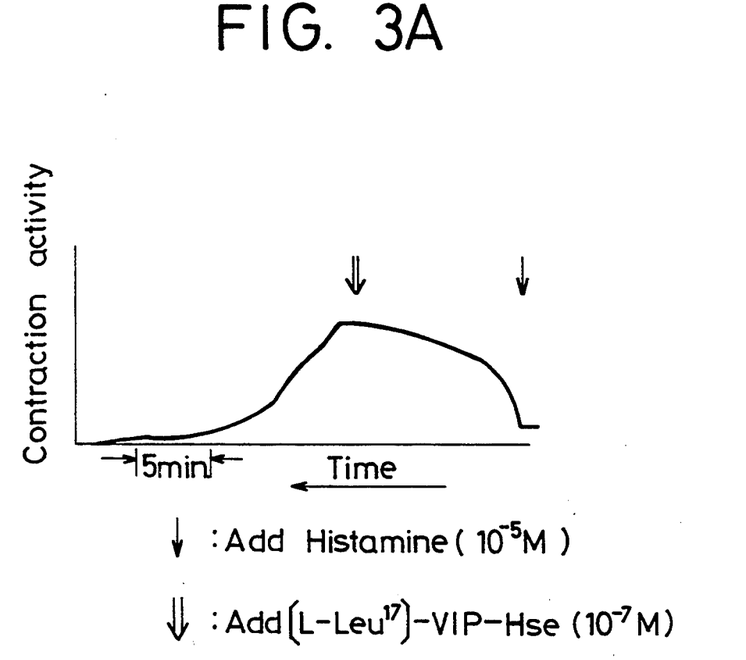
FIG. 3A is a chart showing details of that a bronchus contraction induced by histamine will be atonized by adding a test sample of [L-Leu$^{17}$]-VIP-Hse according to the invention.
Figure 3B:
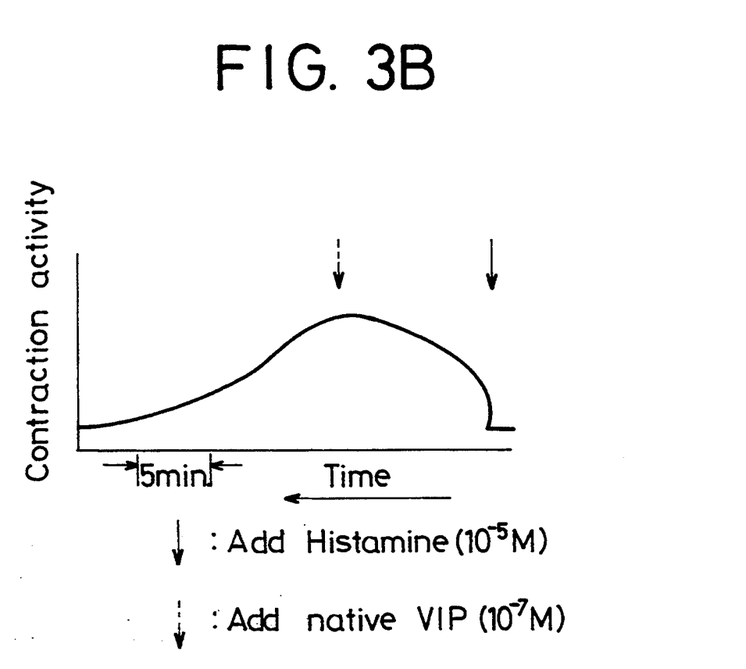
FIG. 3B is a chart similar to FIG. 3, excepting that a control sample of native VIP was added.
Figure 4A:
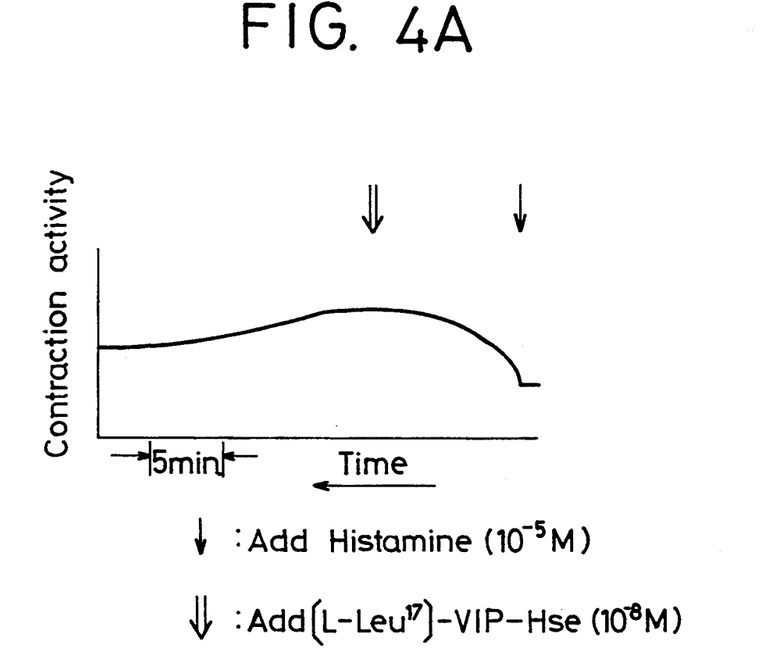
FIGS. 4A and 4B are charts similar to FIGS. 3A and 3B, excepting that concentration of the VIP analogue and native VIP is different.
Figure 4B:
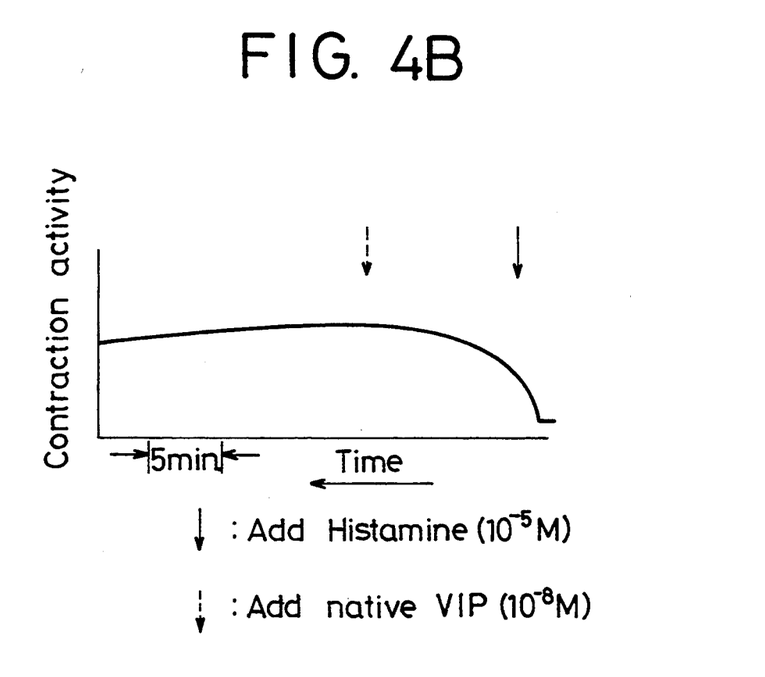

Further, a chart showing reluxant activity of the VIP analogue and native VIP in concentration of 10$^{-7}$M and 10$^{-8}$M are given in FIGS. 3A and 3B as well as FIGS. 4A and 4B, respectively.

It is apparent from the results shown in the Figures, the VIP analogue according to the invention is more excellent than the native VIP.

Pharmacological Test Example 3

(Anti-allergic action)

(1) Preparation of immune serum

A rat was immunized with egg-albumin suspended in aluminum hydroxide gel in a conventional manner and a blood letting was carried out to obtain immune serum rich in IgE.

(2) Passive cutaneous anaphylaxis test (PCA reaction)

A male rat was anethtized with ether and hairs on back were sheared to intradenally inject by 0.1 ml of the immune serum solution described in Item (1) and diluted to 5-folds, at both sides with a certain distance from a medial line on the back. After 72 hours, a mixed solution of egg albumin (5 mg/kg), 2% Evans blue and a test compound ([L-Leu$^{17}$]-VIP-Hse or pure native VIP) or disodium cromoglycate was injected into a vein. After 30 minutes from an occasion of PCA reaction, the experimental animal was killed and pealed-off the skin to obtain a piece of the skin dyed with the coloring matter.

The coloring matter was extracted in accordance with the method described by Katayama ["Microbio. Immunol.", Vol. 22, No. 2, pages 89 (1978)] and an amount thereof was measured at 620 nm in wave length to calculate an inhibition of the PCA reaction.

Results are shown in following Table 1.

TABLE 1

| Dose (mg/kg) | Inhibition (%) | | |
|---|---|---|---|
| | A | B | C |
| 0.01 | 31 | 23 | 5 |
| 0.1 | 79 | 72 | 28 |
| 1.0 | 68 | 67 | 31 |

In the Table,
A: [L-Leu$^{17}$]-VIP-Hse;
B: Native VIP; and
C: Disodium cromoglycate.

Pharmacological Test Example 4

(Hypotensing action)

In a femoral artery of anethtized beagle dog, each of the VIP analogues as Test Samples was injected in a dose of 0.02–10 μg/kg and measured an arterial pressure to prepare a chart showing a relation between the dose and change in blood pressure and check an amount of dose which shall cause a reduction of 15 mmHg in blood pressure.

Following Table 2 shows an effect of the VIP analogues with a relative value, when an amount of dose of native VIP causing a reduction of 15 mmHg in blood pressure shall be made as 100%.

TABLE 2

| Native VIP | 100 (%) |
|---|---|
| [L-Leu$^{17}$]-VIP-Hse | 21 (%) |
| [L-Leu$^{17}$]-VIP-Hse-NH$_2$ | 54 |
| [L-Leu$^{17}$]-VIP-NH(CH$_2$)$_9$CH$_3$ | 68 |

As apparently seen from the Table, the VIP analogues according to the invention show far excellent hypotensing action than the native VIP.

Pharmacological Test Example 5

(Accelerating action on sexual function)

After exenterating testiculus of male rats (mean body weight:about 250 g) to castrate the same, testosterone (4 μg/kg) was continuously injected to each animal over a period of 16 days.

An external cream (Medicine Preparation Example 11 given later and consisting of [L-Leu$^{17}$]-VIP-Hse-NH$_2$, tannic acid and white petrolatum) was applied to a genital organ of each castrated animal (10 μg/animal as [L-Leu$^{17}$]-VIP-Hse-NH$_2$) and each experimental animal was lived in a cage with a female rat she has sexual acceptability, to check and record a number of times of copulation, over a period of 15 minutes.

As to another external cream consisting of [L-Leu$^{17}$]-VIP-Hse-NH$_2$ and white petrolatum, a test similar to the above was carried out.

Results are shown following Table 3.

TABLE 3

| Animal | Control | Test Group A | Test Group B |
|---|---|---|---|
| No. 1 | 9 | 13 | 21 |
| 2 | 6 | 12 | 14 |
| 3 | 3 | 16 | 15 |
| 4 | 7 | 11 | 10 |
| 5 | — | 10 | 13 |
| 6 | 10 | 14 | 17 |

In the Table,
Control: Group applied a cream consisting of white petrolatum only;
Test Group A: Group applied the cream consisting of [L-Leu$^{17}$]-VIP-Hse-NH$_2$ and white petrolatum; and
Test Group B: Group applied the cream consisting of [L-Leu$^{17}$]-VIP-Hse-NH$_2$, tannic acid and white petrolatum.

The result given in the Table shows facts that the VIP analogues strengthen the sexual function, and that the tannic acid provides a rapid or immediate action In some extent.

Pharmacological Test Example 6

(Influence on growth of hair)

Hairs on back of each rabbits (mean body weight:-about 2.5 kg) were cut with an electric hair-clipper and the cut area was shaved. The experimental animals were classified into 6 groups (5 heads for each group). The shaved area was divided into 4 sections. A control solution (aqueous solution of saponin, which contains the saponin in a ratio of 50 mg to 5 ml of water) was applied on the 2 sections and a test solution selected from the followings was applied on remaining 2 sections by an amount of about 0.2 ml/day for each section with an area of 9 cm², over a period of 4 weeks.

Test Solutions

A: Aqueous solution according to Medicine Preparation Example 6 given later and containing [L-Leu$^{17}$]-VIP-NH(CH$_2$)$_9$CH$_3$ and saponin, B: Aqueous solution with a similar prescription to the Solution A excepting that the VIP analogue is [L-Leu$^{17}$]-VIP-Hse, C: Aqueous solution with a similar prescription to the Solution A excepting that the VIP analogue is [L-Leu$^{17}$]-VIP-Hse-NH$_2$, D: Aqueous solution of [L-Leu$^{17}$]-VIP-NH(CH$_2$)$_9$CH$_3$, which contains the VIP analogue in a ratio of 5 mg to water of 5 ml, E: Aqueous solution of [L-Leu$^{17}$]-VIP-Hse, which contains the VIP analogue in a ratio of 5 mg to water of 5 ml, and F: Aqueous solution of [L-Leu$^{17}$]-VIP-Hse-NH$_2$, which contains the VIP analogue in a ratio of 5 mg to water of 5 ml.

On the day after the final application, an accelerating action of hair growth was evaluated under following standards for the judgement.

Standards for judgement

Score, 2 points:

Acceleration of hair growth was recognized in 5 mm or more, in comparison with hairs in the sections where the control solution was applied, Score, 1 point:

Acceleration of hair growth was recognized in less than 5 mm, in comparison with hairs in the sections where the control solution was applied, and Score, 0 (zero) point:

No acceleration of hair growth was recognized, in comparison with hairs in the sections where the control solution was applied.

Results are shown in following Table 4.

TABLE 4

| Test Solutions | Sum of scores |
|---|---|
| A | 9 |
| B | 10· |
| C | 8 |
| D | 4 |
| E | 6 |
| F | 3 |

It is apparent from the Table that each of the VIP analogues according to the invention shows an acceleration of hair growth, and that the coexistence of saponin increases the acceleration.

Pharmacological Test Example 7

(Inhibition of contraction in respiratory tract)

An inhibition of contraction in respiratory tract, which shall be caused by an inhalation of VIP analogues as Test compounds, was checked with use of a guinea pig model of respiratory tract contraction to be induced with an ascaris.

The experimental animals (mean body weight:about 500 g) sensitized with the ascaris were classified into following 4 groups (3 heads for each group).

Control Group

Inhalant: Saline (3 ml),

Test Group A

Inhalant: Saline of a dry powder obtained by Medicine Preparation Example 5 given later, which contains [L-Leu$^{17}$]-VIP-Hse-NH$_2$ of 1 mg/3 ml, Test Group B Inhalant: Saline similar to that for Test Group A, excepting that the VIP analogue is [L-Leu$^{17}$]-VIP-Hse, and Test Group C Inhalant: Saline solution similar to that for Test Group A, excepting that the VIP analogue is [L-Leu$^{17}$]-VIP-Hse-NH(CH$_2$)$_9$CH$_3$.

After giving the inhaltant over a period of 5 minutes to each of the experimental animals in the groups, an ascaris solution (20 mg/3 ml) was given over a period of 3 minutes with use of an inhaler. Measurements of a respiratory resistance and a dynamic compliance, as indexes or the contraction of respiratory tract were carried out by 7 times, namely just before the inhalation of the ascaris solution, Just after the inhalation, and each period of time after 10, 20, 30, 45 and 60 minutes from the inhalation.

Influences of the inhalants for Test Groups to the respiratory resistance and dynamic compliance are given in following Tables 5 and 6 with relative values, when values at just after the inhalation of ascaris solution, and each period of time after 10, 30 and 60 minutes from the inhalation, on the Control Group shall be made as 100%.

TABLE 5

| | (Respiratory Resistance) | | | |
|---|---|---|---|---|
| | Control Group | Test Group A | Test Group B | Test Group C |
| Just after inhalation | 100% | 62% | 59% | 67% |
| After 10 min. | 100% | 65% | 53% | 72% |
| After 30 min. | 100% | 72% | 69% | 80% |
| After 60 min. | 100% | 81% | 78% | 86% |

TABLE 6

| | (Dynamic Compliance) | | | |
|---|---|---|---|---|
| | Control Group | Test Group A | Test Group B | Test Group C |
| Just after inhalation | 100% | 135% | 140% | 132% |
| After 10 min. | 100% | 134% | 141% | 128% |
| After 30 min. | 100% | 136% | 139% | 123% |
| After 60 min. | 100% | 131% | 138% | 115% |

Medicine Preparation Example 1

A solution of the VIP analogue ([L-Leu$^{17}$]-VIP-Hse) in refined water was aseptically charged into vials, so that each vial contains the VIP analogue by 1 mg. After lyophilized, the vial was sealed to obtain a dry powdery medicine. The powdery medicine is dissolved in saline or the like for injection purpose, when it shall be used.

For stabilizing the VIP analogue, a human serum albumin or the like can be used.

Medicine Preparation Examples 2 to 4

Powdery medicines were prepared as described in Medicine Preparation Example 1, excepting that one of the following VIP analogues was employed In lieu of [L-Leu$^{17}$]-VIP-Hse.

a) [L-Leu$^{17}$]-VIP-Hse-NH$_2$,
b) [L-Leu$^{17}$]-VIP-Hse-NH(CH$_2$)$_9$CH$_3$, and
c) [L-Leu$^{17}$]-VIP-Hse-NH(CH$_2$)$_{19}$CH$_3$.

Each of the powdery medicine is dissolved in saline or the like for the injection purpose, when it shall be used. For stabilizing the VIP analogue, a human serum albumin or the like can be used.

Medicine Preparation Example 5

In an aqueous solution (5 ml) consisting of [L-Leu$^{17}$]-VIP-Hse-NH$_2$ (3 mg) and refined water, sodium glycocholate (30 mg) and mannitol (100 mg) were added to dissolve the same. The solution was aseptically charged into a vial. After lyophilized, the vial was sealed to obtain a dry powdery medicine. The powdery medicine is dissolved in refined water and charged into an atomizer or nebulizer to splay the solution into the nasal fossa, when it shall be used.

Medicine Preparation Example 6

In an aqueous solution (5 ml) consisting of [L-Leu$^{17}$]-VIP-Hse-NH(CH$_2$)$_9$CH$_3$ (5 mg) and refined water, saponin (50 mg) was added to dissolve the same. The solution can be dosed to the nasal fossa through an application or spraying.

Medicine Preparation Example 7

A hydrogel type medicine was prepared in a conventional manner and with a following prescription. The medicine was charged into an aluminum tube for packing such type medicine.

| | |
|---|---|
| [L-Leu$^{17}$]-VIP-Hse-NH$_2$ | 300 (mg) |
| Hydroxypropylmethylcellulose | 100 |
| Tween or polysorbate (Note: Trademark) 60 | 100 |
| Gelatin | 500 |
| 70% Aqueous solution of sorbitol | 2000 |
| Citric acid | 100 |
| Disodium hydrogenphosphate | 300 |
| Sodium chloride | 500 |
| Benzalkonium chloride | 20 |
| Refined water | remainder |
| Total | 100 (g) |

Medicine Preparation Example 8

To prepare a granular preparation off 1 g in dose for each time, [L-Leu$^{17}$]-VIP-Hse-NH$_2$ (10 mg) and sucrose palmitate (200 mg) were mixed. To the mixture, lactose, starch and hydroxypropylcelluose were added in a suitable amount to prepare granules in a conventional manner. Then, an enteric coating was applied thereto with use of hydroxypropylmethylcellulose (P).

Medicine Preparation Example 9

Tablets were prepared in a conventional manner and with a following prescription.

| | |
|---|---|
| [L-Leu$^{17}$]-VIP-Hse | 10 (mg) |
| Sodium laurylsulfate | 20 |
| Carboxymethylcellulose (Ca) | 7 |
| Crystalline cellulose | 2 |
| Magnesium stearate | 7 |
| Lactose | remainder |
| Total | 200 (mg)/tablet |

Medicine Preparation Example 10

A suppositories were prepared in a conventional manner and with a following prescription.

| | |
|---|---|
| [L-Leu$^{17}$]-VIP-Hse | 20 (mg) |
| Tannic acid | 30 |
| Ichthamol | 300 |
| Cacao butter | remainder |
| Total | 1000 (mg)/piece |

Medicine Preparation Example 11

An external cream or ointment was prepared in a conventional manner and with a following prescription.

| | |
|---|---|
| [L-Leu$^{17}$]-VIP-Hse-NH$_2$ | 100 (mg) |
| Tannic acid | 100 |
| White petrolatum | remainder |
| Total | 100 (g) |

Medicine Preparation Example 12

An ophthalmic solution was prepared in a conventional manner and with a following prescription.

| | |
|---|---|
| [L-Leu$^{17}$]-VIP-Hse | 1000 (mg) |
| Sodium dihydrogenphosphate (anhydride) | 560 |
| Disodium hydrogenphosphate (anhydride) | 370 |
| Sodium chloride | 370 |
| Benzalkonium chloride solution | remainder |
| (diluted to 1/50000) | |
| Total | 100 (ml) |

---

What is claimed is:

1. A vasoactive intestinal polypeptide (VIP) analogue selected from the group consisting of [L-Leu$^{17}$]-VIP-Hse, [L-Leu$^{17}$]-VIP-Hse-lactone, [L-Leu$^{17}$]-VIP-Hse-NH$_2$, [L-Leu$^{17}$]-VIP-Hse-NH(CH$_2$)$_9$CH$_3$ and [L-Leu$^{17}$]-VIP-Hse-NH(CH$_2$)$_{19}$CH$_3$.

2. A pharmaceutical composition comprising an effective amount of a vasoactive intestinal polypeptide (VIP) analogue selected from the group consisting of [L-Leu$^{17}$]-VIP-Hse, [L-Leu$^{17}$]-VIP-Hse-lactone, [L-Leu$^{17}$]-VIP-Hse-NH$_2$, [L-Leu$^{17}$]-VIP-Hse-NH(CH$_2$)$_9$CH$_3$ and [L-Leu$^{17}$]-VIP-Hse-NH(CH$_2$)$_{19}$CH$_3$, in combination with a pharmaceutically acceptable carrier.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 28 amino acids
( B ) TYPE: amino acid
( D ) TOPOLOGY: linear -continued (ii) MOLECULE TYPE: peptide (v) FRAGMENT TYPE: C-terminal (vi) ORIGINAL SOURCE:
    (A) ORGANISM: Homo sapiens
    (F) TISSUE TYPE: Small intestine, proximal (xi) SEQUENCE DESCRIPTION: SEQ ID NO:1:

```
His Ser Asp Ala Val Phe Thr Asp Asn Tyr Thr Arg Leu Arg Lys Gln
1               5                   10                      15

Met Ala Val Lys Lys Tyr Leu Asn Ser Ile Leu Asn
            20                  25
```

(2) INFORMATION FOR SEQ ID NO:2:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:2:

```
His Ser Asp Ala Val Phe Thr Asp Asn Tyr Thr Arg Leu Arg Lys Gln
1               5                   10                      15

Xaa Ala Val Lys Lys Tyr Leu Asn Ser Ile Leu Asn
            20                  25
```

(2) INFORMATION FOR SEQ ID NO:3:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (xi) SEQUENCE DESCRIPTION: SEQ ID NO:3:

```
His Ser Asp Ala Val Phe Thr Asp Asn Tyr Thr Arg Leu Arg Lys Gln
1               5                   10                      15

Leu Ala Val Lys Lys Tyr Leu Asn Ser Ile Leu Asn Met Ala Ser
            20                  25                  30
```

(2) INFORMATION FOR SEQ ID NO:4:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (xi) SEQUENCE DESCRIPTION: SEQ ID NO:4:

```
His Ser Asp Ala Val Phe Thr Asp Asn Tyr Thr Arg Leu Arg Lys Gln
1               5                   10                      15

Leu Ala Val Lys Lys Tyr Leu Asn Ser Ile Leu Asn Xaa
            20                  25
```